United States Patent [19]

Stegmann

[11] Patent Number: 4,691,058

[45] Date of Patent: Sep. 1, 1987

[54] PROCESS FOR PRODUCING 1-HYDROXY KETONES

[75] Inventor: Werner Stegmann, Liestal, Switzerland

[73] Assignee: Ciba-Geigy Corporation, Ardsley, N.Y.

[21] Appl. No.: 701,792

[22] Filed: Feb. 14, 1985

Related U.S. Application Data

[63] Continuation of Ser. No. 488,936, Apr. 27, 1983, abandoned.

[30] Foreign Application Priority Data

May 7, 1982 [CH] Switzerland ............... 2842/82

[51] Int. Cl.$^4$ ............................................. C07C 45/64
[52] U.S. Cl. ................................................ 568/316
[58] Field of Search ............................. 568/316, 891

[56] References Cited

U.S. PATENT DOCUMENTS 4,308,400 12/1981 Felder et al. ............... 568/316
4,347,111 8/1982 Gehlhaus et al. ........... 568/316

FOREIGN PATENT DOCUMENTS 2808459 8/1979 Fed. Rep. of Germany ...... 562/316

OTHER PUBLICATIONS

Meyer, Hoube–Weyl, vol. VII/2C, pp. 2173-2243, (1977).
Dehmlow et al, "Phase Transfer Catalysis", Verlog Chemie, p. 155, (1980).

Primary Examiner—James H. Reamer
Attorney, Agent, or Firm—Luther A. R. Hall

[57] ABSTRACT

The invention relates to a novel process for producing compounds of the formula I

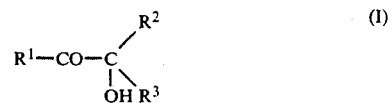

in which $R^1$ is for example phenyl, and $R^2$ and $R^3$ are for example cyclohexyl. With application of the phase-transfer catalysis method, a corresponding compound of the formula II

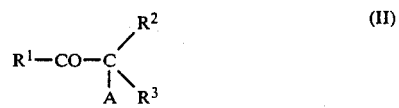

is reacted, in the presence of water, with hydroxide ions, especially with alkali metal hydroxide or alkaline-earth metal hydroxide.

11 Claims, No Drawings

PROCESS FOR PRODUCING 1-HYDROXY KETONES

This is a continuation of application Ser. No. 488,936, filed on Apr. 27, 1983, now abandoned.

The invention relates to a novel process for producing 1-hydroxy ketones.

It is well known that 1-hydroxy ketones are effective initiators for the photopolymerisation of unsaturated compounds, and also effective photochemical crosslinking agents for polyolefins. Such applications are described for example in the EP Patent Specification No. 3002.

According to a known process for producing 1-hydroxy ketones, the corresponding α-haloketones are converted by direct hydrolysis, or by hydrolysis via the stage of the corresponding formic acid ester or acetic acid ester, into the desired products. Reference is made in this connection for example to a publication of D. Mayer "Hydroxy ketones and esters thereof" in Houben-Weyl, Vol. VII/2c, pp 2171-2243, (1977). This known process however has considerable disadvantages. It is for instance adversely affected by base-catalysed isomerisation of the α-hydroxy ketones, and a consequently impure final product in only moderate yield is obtained. In the above publication, there is emphasised, as a further complication with this type of reaction, the possibility of Faworsky rearrangements, which likewise result in an isomeric mixture that contains, besides the desired hydroxy ketone, also the isomeric carboxylic acid.

A further known process for producing 1-hydroxy ketones is also described in the aforementioned publication on page 2177ff. Haloepoxides are hydrolysed in an acid or aliphatic medium. This process too has the disadvantage that the yield is low, and that considerably impure final products occur.

It is also to be particularly emphasised that the technical expenditure required for all the known processes is extremely high.

The process according to the present invention surprisingly does not have the disadvantages of the known processes for producing 1-hydroxy ketones. Very pure products in high yield are obtained; and the technical equipment for carrying out the novel process is simple and low in cost.

Subject matter of the present invention is thus a process for producing a compound of the formula I

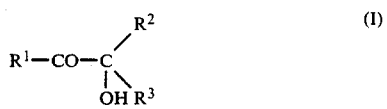

in which $R^1$ is a phenyl group which can be substituted by straight-chain or branched-chain $C_1$-$C_4$-alkyl groups, $R^2$ and $R^3$ are identical or different, and are each a straight-chain or branched-chain $C_1$-$C_5$-alkyl group, or a $C_5$-$C_8$-cycloalkyl group which can be substituted by 1 to 3 straight-chain or branched-chain $C_1$-$C_5$-alkyl groups, or together with the C atom to which they are bound they form a $C_5$-$C_8$-cycloalkyl group which can be substituted by 1 to 3 straight-chain or branched-chain $C_1$-$C_4$-alkyl groups, the process comprising the reaction of a compound of the formula II

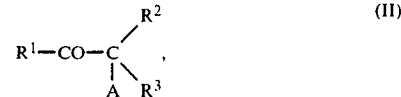

in which $R^1$, $R^2$ and $R^3$ are as defined above, and A is chlorine or bromine, preferably chlorine, with a compound releasing hydroxide ions, in the presence of water or in the presence of water and an inert organic solvent, by the phase-transfer catalysis method, whereby the compound of the formula II is present in solution or in the melted state.

Besides being phenyl, $R^1$ can be in particular an o-, m- or p-toluyl or -xylyl group. $R^2$ and/or $R^3$ can be for example the following alkyl groups: methyl, iso-propyl, n-butyl, sec-butyl, tert-butyl or tert-pentyl. As cycloalkyl groups, they can be for example: cyclopentyl, cyclohexyl, cycloheptyl or cyclooctyl. Cyclopentyl and cyclohexyl are preferred.

When $R^2$ and $R^3$ together with the C atom to which they are bound form a cycloalkyl group, they can be the same as those already mentioned.

There are preferably produced compounds of the formula I wherein $R^1$ is a phenyl group unsubstituted or substituted by one or more $C_1$-$C_4$-alkyl groups, $R^2$ and $R^3$ are each methyl, or together with the C atom to which they are bound they are cyclohexyl, by reacting corresponding compounds of the formula II with compounds releasing hydroxide ions.

A particularly preferred embodiment of the invention comprises the production of a compound from the series of the formulae

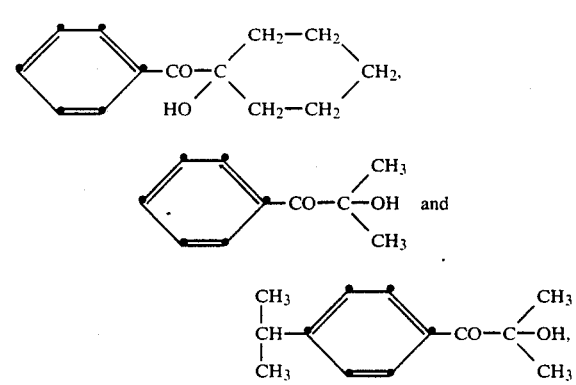

whereby the corresponding compound of the formula II used is 1-chlorocyclohexyl-phenyl ketone, 1-chloroisopropylphenyl ketone or 1-chloroisopropyl-4, -isopropyl-phenyl ketone.

The reaction according to the invention is performed preferably at temperatures of between 0° and 120° C., especially between 60° and 85° C.

Reaction times of 2 to 5 hours, preferably about 3 hours, are necessary for the obtainment of good results.

According to a preferred embodiment of the invention, the compound of the formula II is present in the melted form in the reaction mixture, and the reaction is performed in the absence of inert organic solvents.

If inert organic solvents are used, they are e.g. aromatic hydrocarbons, such as benzene, toluene, xylenes, aliphatic or cycloaliphatic hydrocarbons, such as heptane, hexane or ligroin, also ketones, esters or ethers and glycol ethers.

Compounds releasing hydroxide ions are for example alkali metal hydroxides or alkaline-earth metal hydroxides. The amount used is preferably 100–150% by weight of the theoretical amount. The compounds of the formula II are preferably reacted with KOH or NaOH.

The compounds releasing hydroxide ions are advantageously used in the form of aqueous solutions, so that the halide salt forming in the course of the reaction remains in solution in the reaction medium.

Preferred as phase transfer catalysts are compounds of the formula III

in which $R^a$, $R^b$, $R^c$ and $R^d$ are identical or different, and are straight-chain or branched-chain alkyl groups, where all 4 alkyl groups together have 4 to 20 C atoms, or they are benzyl, and $X^\ominus$ is $-HSO_4^\ominus$ or $-Cl^\ominus$.

$R^a$, $R^b$, $R^c$ and $R^d$ can be the following alkyl groups: for example methyl, iso-propyl, n-butyl, sec-butyl, tert-butyl, tert-pentyl, 2-ethylhexyl, n-octyl, 1,1,3,3-tetramethylbutyl or n-dodecyl.

The amount of catalyst used can be freely chosen; it is however preferably 0.1–2 mol %, relative to 1 mol of the compound of the formula II.

Catalysts particularly preferably used are the compounds from the following series:

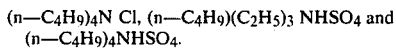

According to a preferred embodiment of the invention, the phase transfer catalyst used is a compound of the formula III bound to a polymeric solid resin. Suitable polymeric solid resins are in particular organic high-polymers based on polystyrene.

Especially advantageous according to the invention is a very vigorous stirring of the reaction mixture, by virtue of which are obtained high yields and corresponding degrees of purity of the final products. The use of an impeller stirrer with current interrupter has proved to be particularly suitable for this purpose. Examples of intensive mixers or stirrers are: inclined blade mixers and disc mixers, multi-stage impulse countercurrent stirrers, such as MIG ®, interference multi-stage impulse countercurrent stirrers, such as INTERMIG ®, and also spiral mixers and beam-control mixers.

The compounds of the formula II used as starting products are known, and they are produced by known methods. Reference is made in this connection to the already mentioned publication of D. Mayer "Hydroxyketone und deren Ester" (Hydroxy ketones and esters thereof) in Houben-Weyl, Vol. VII/2c, to the EP Patent Specification No. 3002, and to the book of H.O. House: "Modern Synthetic Reactions" (p. 459ff) (Publishers Bejamin 1972).

The present invention is further illustrated by the following Examples.

EXAMPLE 1

A mixture of 282 g of 1-chlorocyclohexyl-phenyl ketone, 156 g of water and 156 g of potassium hydroxide (50%) solution) is heated to 60°–65° C. in a vessel with a glass stirrer and with a reflux condenser, whereupon the 1-chlorocyclohexyl-phenyl ketone melts. A solution of 0.4 g of tetrabutylammonium hydrogen sulfate in 6 g of water is added portionwise within 30 minutes. The temperature of the reaction mixture is held at 60°–75° C. After the reaction has subsided, a further 1.7 g of tetrabutyl-ammonium hydrogen sulfate, dissolved in 25 g of water, are added portionwise during 30 minutes, the temperature being maintained at 65°–75° C. The reaction mixture is heated to 80° C., and is stirred at this temperature for about 3 hours. No further educt can then be identified (content of 1-chlorocyclohexylphenyl ketone $\leq 0.1\%$, DC evidence). After separation of the aqueous phase at 70° C., 170 g of water are added to the product melt, and the pH value of the water phase is adjusted to 5.5–7 by the addition of about 0.2 g of acetic acid. After stirring, the aqueous phase is separated, and the organic melt is again washed with 170 g of water. An addition of 100 g of toluene is made, and the water is removed by azeotropic distillation. The yield after the residual amount of toluene has been distilled off at 110° C./$1.6 \cdot 10^3$ Pa is about 257 g of crude 1-hydroxycyclohexyl-phenyl ketone, corresponding to 99% of theory. The product slowly crystallises out from the melt, m.p. 45°–49° C.

EXAMPLE 2

66.8 g of 1-chlorocyclohexyl-phenyl ketone and 26.4 g of 50% sodium hydroxide are heated to 60°–65° C., and to the solution/melt are added, with rapid stirring, 2 g of tetrabutylammonium hydrogen sulfate, dissolved in 10 g of water. The temperature of the reaction mixture rises to about 85° C., and after the mixture has been stirred for three hours at 80° C. the reaction has finished (content of 1-chlorocyclohexylphenyl ketone in the reaction mixture 0.1%; DC evidence). The reaction mixture is stirred with 50 ml of toluene and 60 g of water for 10 minutes at about 60° C., and the lower aqueous phase is then separated. To the toluene solution are added 60 g of water, and the pH value is adjusted to 7 with a few drops of diluted hydrochloric acid; and, after the separation of the aqueous phase, the toluene solution is washed at 60° C. twice with 50 g of water each time. After the toluene has been distilled off at 90° C./$2.67 \cdot 10^3$ Pa, there remain about 60.5 g of crude product (98.5% of theory): the crude product, 1-hydroxycyclohexyl-phenyl ketone, has a content of 98.4%, determined by gas chromatographic analysis.

EXAMPLE 3

66.8 g of 1-chlorocyclohexyl-phenyl ketone and 37 g of 50% potassium hydroxide are heated to 60°–65° C., and, with rapid stirring, 1.7 g of tetrabutyl-ammonium chloride, dissolved in 10 g of water, are added, the temperature then rising to about 100° C. The reaction is complete after two hours' stirring at 90°–70° C., and further processing is carried out in the manner described in EXAMPLE 2: yield=58.5 g of 1-hydroxycyclohexyl-phenyl ketone=95.5% of theory; content: 98.8%, determined by gas-chromatography (GC).

EXAMPLE 4

A mixture of 66.8 g of 1-chlorocyclohexyl-phenyl ketone and 37 g of potassium hydroxide (50% aqueous solution) is taken into solution or melted by being heated to 60°–65° C. A solution of 1.73 g of benzyl-triethyl-ammonium hydrogen sulfate in 10 g of water is rapidly added, whereupon the temperature rises to 90° C., and the reaction is finished after the mixture has been stirred for three and a half hours at 60° C. The yield after further processing as in Example 2 is 38.5 g of 1-hydroxycyclohexyl-phenyl ketone (63% of theory); content=97.4% (GC).

EXAMPLE 5

A mixture of 66.8 g of 1-chlorocyclohexyl-phenyl ketone and 38.2 g of 50% potassium hydroxide is heated to 60°-65° C. 1.1 g of tetramethylammonium hydrogen sulfate, dissolved in 10 g of water, are added all at once, whereupon the temperature rises by about 7° C.; and the reaction mixture is then stirred for 3 hours at 60° C. After the addition of 10 g of water, the mixture is stirred for 5 hours at 80° C. and subsequently for 5 hours at 100° C., until the final point of the reaction is reached. Further processing as in Example 2 yields about 50 g of crude product: 1-hydroxycyclohexyl-phenyl ketone (81% of theory); content=97.4% (GC).

EXAMPLE 6

A mixture of 66.8 g of 1-chlorocyclohexyl-phenyl ketone and 38.2 g of 50% potassium hydroxide is heated to 60°-65° C. 2.7 g of tetrahexylammonium hydrogen sulfate, dissolved in 10 g of water, are quickly added with vigorous stirring, whereupon the internal temperature rises to 108° C. After being stirred at 60° C. for two hours, the reaction mixture is further processed as in Example 2; yield=55 g of 1-hydroxycyclohexyl-phenyl ketone (90% of theory); content: 91.5% (GC).

EXAMPLE 7

A mixture of 133.6 g of 1-chlorocyclohexyl-phenyl ketone, 244 ml of heptane, 69.4 g of potassium hydroxide (50%), 20 g of water and 4 g of tetrabutylammonium hydrogen sulfate is heated to 80° C., and is stirred for 8 hours at this temperature. There remains after this time less than 0.2% of 1-chlorocyclohexyl-phenyl ketone in the reaction mixture. After the addition of 60 g of water, the mixture is stirred at 50°-60° C. for 10 minutes, and the aqueous layer is then separated. The heptane solution is washed four times with 60 g of water each time; it is subsequently cooled, and, with the addition of seed crystals, it is crystallised at 15°-20° C. The suspension is cooled to 0° to 3° C., and is filtered after being stirred for one hour. The suction-filter residue is washed twice with 60 ml of ice-cold heptane each time, and then dried at 30°-40° C. in vacuo. The yield of 1-hydroxycyclohexylphenyl ketone is 97.5 g (79.6% of theory); m.p. 46°-49° C.

EXAMPLE 8

A mixture of 160.3 g of 1-bromocyclohexylphenyl ketone, 80.8 g of 50% potassium hydroxide and 51 g of water is heated to 60°-65° C., and to this solution is added 0.2 g of tetrabutylammonium hydrogen sulfate, dissolved in 3 g of water. The reaction mixture is subsequently held at 60°-70° C. for one hour; to this solution at 70° C. is added a further 0.8 g of tetrabutylammonium hydrogen sulfate, dissolved in 12 ml of water, and the reaction mixture is then stirred at 75°-80° C. for three hours, after which time no further educt is detectable (content of 1-bromocyclohexyl-phenyl ketone ≦0.1%, DC evidence). After separation of the aqueous phase at 60° C., there are added to the product melt 51 g of water, and the mixture is stirred at 60°-70° C. for 10 minutes. The pH value of the aqueous phase is adjusted to about 7 by the addition of 1 ml of 80% acetic acid. The aqueous phase is separated, and the product melt is again washed with 51 g of water. To the crude product thus obtained are added 185 g of heptane isomeric mixture and 3.7 g of active charcoal, and the mixture is stirred at 45°-55° C. for 30 minutes. After filtration until clear, the product solution is cooled to 22° C. and is then injected with seed crystals. The resulting suspension is cooled to −5° to −10° C., and the product is filtered off. The suction-filter residue is washed with a total of 155 g of heptane at 0° to −10° C. The yield after drying at 30°-40° C. in vacuo is 80.4 g of 1-hydroxycyclohexyl-phenyl ketone, corresponding to 66% of theory; melting range: 43°-48° C.

EXAMPLE 9

A mixture of 135.8 g of 4′-isopropylphenyl-(1-chloroisopropyl) ketone, 80.8 g of 50% potassium hydroxide and 51 g of water is heated to 60° C. After the addition of a solution of 0.2 g of tetrabutylammonium hydrogen sulfate in 3 g of water, stirring is maintained for 30 minutes at 60°-70° C. Into this solution at 70° C. is introduced 0.8 g of tetrabutylammonium hydrogen sulfate, dissolved in 12 g of water, and the reaction mixture is stirred at 75°-85° C. for 5 hours. The aqueous phase is afterwards separated at 80° C., and to the organic phase is added a mixture of 40 g of 50% potassium hydroxide, 51 g of water and 1 g of tetrabutylammonium hydrogen sulfate, dissolved in 15 g of water. After stirring at 70°-80° C. for 1 hour, there is, according to thin-layer chromatographic analysis, no further educt detectable (detection limit 0.1%); and the aqueous phase is then separated at 60° C. After the addition of 51 g of water to the organic phase remaining, the pH value is adjusted to about 7 with 1 ml of 80% acetic acid, and the aqueous phase is subsequently separated. To the organic phase are added 100 g of toluene, the mixture is azeotropically dehydrated, and the toluene is distilled off at 90° C./$1.9 \cdot 10^3$ Pa. The yield is 121 g of 4′-isopropyl-phenyl-(1-hydroxyisopropyl) ketone, corresponding to 98.6% of theory, with a boiling point of 164° C./$3.7 \cdot 10^3$ Pa. IR Spectrum in 2% CCl$_4$ solution; absorption bands in cm$^{-1}$: 1655 [>C=O]; 2780, 2955 and 3460 [—OH].

EXAMPLE 10

155 g of 1-chloroisopropyl-phenyl ketone, 115 g of aqueous 50% potassium hydroxide solution, 73 g of water and 0.3 g of tetrabutylammonium hydrogen sulfate, dissolved in 4.5 g of water, are heated to 80° C. with stirring. The reaction mixture is stirred for 30 minutes at 80° C., and a further 1.2 g of tetrabutylammonium hydrogen sulfate, dissolved in 17 g of water, are added. The mixture is stirred for 1 hour at 70°-80° C., a further 50 g of water are added, and the aqueous phase is then separated. To the product melt are added 75 g of water, and the mixture is stirred at 60°-70° C. for 10 minutes. The pH value is adjusted with about 5 g of 80% acetic acid to 7. The lower aqueous phase is separated, and the product is washed again with 73 g of water. 5.3 g of active charcoal and 262 g of heptane are added to the product melt, and stirring is maintained at 50°-60° C. for 10 minutes. After filtration of the active charcoal and removal of the heptane by distillation at 80° C./$2.6 \cdot 10^3$ Pa in a rotary evaporator, the yield is 130 g of 1-hydroxyisopropyl-phenyl ketone, corresponding to 93% of theory; boiling point: 134° C./$3.3 \cdot 10^3$ Pa; IR spectrum in 2% CCl$_4$ solution; absorption bands in cm$^{-1}$ at: 1655 [>C=O]; 2950 and 3450 [—OH].

EXAMPLE 11

150 g of 4'-chlorophenyl-1-chloroisopropyl ketone, 93 g of 50% aqueous potassium hydroxide solution and 70 g of water are heated to 60° C. with stirring. After the addition of 0.23 g of tetrabutylammonium hydrogen sulfate, dissolved in 4.1 g of water (exothermic reaction), stirring is continued for 30 minutes at 65°–70° C.; there is then added a further 0.93 g of tetrabutylammonium hydrogen sulfate, dissolved in 16.5 g of water, and the mixture is stirred at 70°–80° C. for 1 hour. After the separation of the lower aqueous phase at 60° C., 70 g or water are added; the mixture is subsequently stirred up for 10 minutes, and the pH-value is adjusted to about 7 by the addition of about 3 g of 80% acetic acid. The upper aqueous phase is separated, and the product is again washed at 60°–70° C. with 70 g of water. To the organic phase are added 5.1 g of active charcoal and 52 g of heptane, and stirring is maintained at 50°–55° C. for 10 minutes. The suspension is filtered clear through Hyflo, and the heptane is distilled off at 80° C./$2.7 \cdot 10^3$ Pa. The yield is 128.6 g of 4'-chlorophenyl-1-hydroxyisopropyl ketone, corresponding to 93.7% of theory: boiling point: 147° C./$2.2 \cdot 10^3$ Pa; IR spectrum in 2% CCl$_4$ solution: absorption bands in cm$^{-1}$ at: 1660 [C=O]; 2950 and 3450 [—OH].

What is claimed is:

1. A process for producing a compound of the formula I

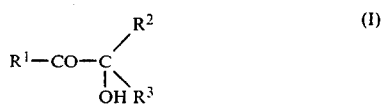

in which $R^1$ is phenyl or said phenyl substituted by straight-chain or branched-chain $C_1$-$C_4$-alkyl groups, $R^2$ and $R^3$ are identical or different, and are each a straight-chain or branched chain $C_1$-$C_5$-alkyl group, or a $C_5$-$C_8$-cycloalkyl or said cycloalkyl substituted by 1 to 3 straight-chain or branched chain $C_1$-$C_5$-alkyl groups, or together with the C atom to which they are bound they form a $C_5$-$C_8$-cycloalkyl or said cycloalkyl substituted by 1 to 3 straight-chain or branched-chain $C_1$-$C_4$-alkyl groups, which process comprises reacting a compound of formula II

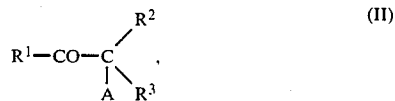

in which $R^1$, $R^2$ and $R^3$ are as defined above, and A is chlorine or bromine, with a compound releasing hydroxide ions, in the presence of water or in the presence of water and an inert organic solvent, by the phase-transfer catalysis method, whereby the compound of the formula II is present in solution or in the melted form.

2. A process according to claim 1, wherein A in the formula II is chlorine.

3. A process according to claim 1, wherein there is produced a compound of the formula I wherein $R^1$ is a phenyl or said phenyl substituted by one or more $C_1$-$C_4$-alkyl groups, $R^2$ and $R^3$ are each methyl, or together with the C atom to which they are bound they are cyclohexyl, which process comprises reacting a corresponding compound of the formula II with a compound releasing hydroxide ions.

4. A process according to claim 1, wherein an alkali metal hydroxide or alkaline-earth metal hydroxide is reacted as the compound releasing hydroxide ions.

5. A process according to claim 1, wherein KOH or NaOH is reacted as the compound releasing hydroxide ions.

6. A process according to claim 5, wherein the compound KOH or NaOH is used in the form of an aqueous solution.

7. A process according to claim 1, wherein the compound of the formula II is present in the melted form in the reaction mixture, and in the absence of inert organic solvents.

8. A process according to claim 1, wherein the employed phase-transfer catalyst is a compound of the formula III $$(R^a)(R^b)(R^c)(R^d) N \oplus X \ominus \qquad \text{(III)},$$

in which $R^a$, $R^b$, $R^c$ and $R^d$ are identical or different, and are straight-chain or branched-chain alkyl groups, where all 4 alkyl groups together have 4 to 20 C atoms, or they are benzyl, and $X\ominus$ is —HSO$_4\ominus$ or —Cl$\ominus$.

9. A process according to claim 8, wherein the phase-transfer catalyst used is any compound from the series: (n—C$_4$H$_9$)$_4$N Cl, (n—C$_4$H$_9$)(C$_2$H$_5$)$_3$NHSO$_4$ and (n—C$_4$H$_9$)$_4$NHSO$_4$.

10. A process according to claim 8, wherein the phase-transfer catalyst used is a compound of the formula III bound to a polymeric solid resin.

11. A process according to claim 1, wherein there is produced a compound selected from the group consisting of the formulae

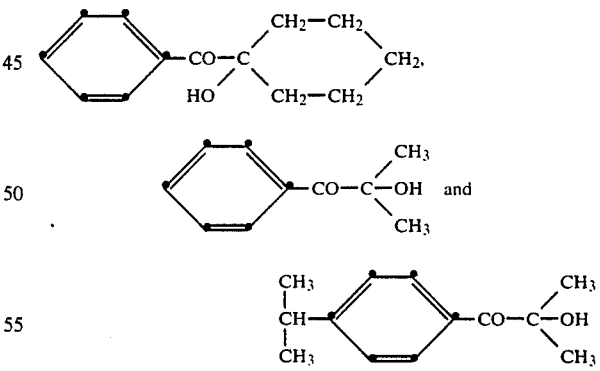

by using, as a corresponding compound of the formula II: 1-chlorocyclohexyl-phenyl ketone, 1-chloroisopropylphenyl ketone or 1-chloroisopropyl-4'-isopropylphenyl ketone.

* * * * *